US012760014B2

(12) United States Patent
Wang et al.

(10) Patent No.: US 12,760,014 B2
(45) Date of Patent: Oct. 13, 2026

(54) SUCCINATE AND CRYSTAL FORM THEREOF AS THERAPEUTICS

(71) Applicant: AUCENTRA THERAPEUTICS PTY LTD, Adelaide (AU)

(72) Inventors: Shudong Wang, Adelaide (AU); Hui Wang, Changzhou (CN); Jinchen Lv, Changzhou (CN); Jun Liu, Changzhou (CN)

(73) Assignee: AUCENTRA THERAPEUTICS PTY LTD, Adelaide (AU)

( * ) Notice: Subject to any disclaimer, the term of this patent is extended or adjusted under 35 U.S.C. 154(b) by 510 days.

(21) Appl. No.: 18/036,224

(22) PCT Filed: Nov. 10, 2021

(86) PCT No.: PCT/AU2021/051325
§ 371 (c)(1),
(2) Date: May 10, 2023

(87) PCT Pub. No.: WO2022/099357
PCT Pub. Date: May 19, 2022

(65) Prior Publication Data

US 2023/0399325 A1 Dec. 14, 2023

(30) Foreign Application Priority Data

Nov. 10, 2020 (CN) ......................... 202011249267.6

(51) Int. Cl.
*C07D 417/14* (2006.01)
*A61P 35/00* (2006.01)

(52) U.S. Cl.
CPC ............ *C07D 417/14* (2013.01); *A61P 35/00* (2018.01); *C07B 2200/13* (2013.01)

(58) Field of Classification Search
CPC .... A61P 35/00; C07D 417/14; C07B 2200/13
See application file for complete search history.

(56) References Cited

U.S. PATENT DOCUMENTS

| | | | | |
|---|---|---|---|---|
| 9,062,039 | B2 | 6/2015 | Wang et al. | |
| 10,479,785 | B2 * | 11/2019 | Wang .................. | C07D 417/14 |
| 2006/0241297 | A1 | 10/2006 | Wang et al. | |

FOREIGN PATENT DOCUMENTS

| | | | |
|---|---|---|---|
| CN | 102143953 | A | 8/2011 |
| CN | 103373994 | A | 10/2013 |
| CN | 107787226 | A | 3/2018 |
| CN | 108349964 | A | 7/2018 |
| CN | 108658966 | A | 10/2018 |

OTHER PUBLICATIONS

Berge et al., J. Pharm. Sci. 66:1-19 (1977) (Year: 1977).*

Bastin, Richard J., Michael J. Bowker, and Bryan J. Slater. "Salt selection and optimisation procedures for pharmaceutical new chemical entities." Organic Process Research & Development 4, No. 5 (2000): 427-435 (Year: 2000).*

Thorson, M.R., Goyal, S., Schudel, B.R., Zukoski, C.F., Zhang, G.G., Gong, Y. and Kenis, P.J., 2011. A microfluidic platform for pharmaceutical salt screening. Lab on a Chip, 11(22), pp. 3829-3837 (Year: 2011).*

Tadesse et al.2017. Highly potent, selective, and orally bioavailable 4-thiazol-N-(pyridin-2-yl) pyrimidin-2-amine cyclin-dependent kinases 4 and 6 inhibitors as anticancer drug candidates: design, synthesis, and evaluation. Journal of Medicinal Chemistry, 60(5), pp. 1892-1915 (Year: 2017).*

International Search Report and Written Opinion in Application No. PCT/AU2021/051325, mailed Jan. 4, 2022, 8 pages.

Tadesse, S. et al., "Highly Potent, Selective, and Orally Bioavailable 4-Thiazol-N-(pyridin-2-yl)pyrimidin-2-amine Cyclin-Dependent Kinases 4 and 6 Inhibitors as Anticancer Drug Candidates: Design, Synthesis, and Evaluation", Journal of Medicinal Chemistry. 2017, vol. 60, pp. 1892-1915.

* cited by examiner

*Primary Examiner* — James H Alstrum-Acevedo
*Assistant Examiner* — Carolyn L. Ladd
(74) *Attorney, Agent, or Firm* — Meunier Carlin & Curfman LLC

(57) ABSTRACT

Disclosed are salts of N-Cyclopentyl-5-(2-((5-((4-ethylpiperazin-1-yl)methyl)pyridin-2-yl)amino)-5-fluoropyrimidin-4-yl)-4-methylthiazol-2-amine and polymorphs thereof, which are inhibitors of protein kinases, in particular cyclin-dependent kinase 4/6 (CDK4/6), and can be used to treat proliferative disorders, such as cancer, and other diseases related to protein kinase/CDK activity. The disclosure includes the succinate salt of N-cyclopentyl-5-(2-((5-((4-ethylpiperazin-1-yl)methyl)pyridin-2-yl)amino)-5-fluoropyrimidin-4-yl)-4-methylthiazol-2-amine, Crystal Form A of the succinate salt, a pharmaceutical formulation comprising the succinate salt, and use of the succinate salt to treat the proliferative disorders.

12 Claims, 11 Drawing Sheets

SUCCINATE AND CRYSTAL FORM THEREOF AS THERAPEUTICS

TECHNICAL FIELD

The present invention relates to pharmaceutical salts of N-Cyclopentyl-5-(2-((5-((4-ethylpiperazin-1-yl)methyl) pyridin-2-yl)amino)-5-fluoropyrimidin-4-yl)-4-methylthiazol-2-amine and crystal forms thereof, which are inhibitors of Cyclin-Dependent Kinases (CDKs), such as CDK4/6, and which may be used to treat proliferative disorders, such as cancer.

PRIORITY DOCUMENT

The present application is a United States National Phase Patent Application of International Patent Application Number PCT/AU/2021/051325, filed Nov. 10, 2021, which claims the benefit of priority to Chinese Patent Application No. 202011249267.6 titled "Succinate and crystal form thereof as selective CDK4/6 Inhibitors" and filed on Nov. 10, 2020, the content of which is hereby incorporated by reference in their entirety.

BACKGROUND

There is an ongoing need to identify and develop new compounds for treating proliferative diseases and conditions including cancers. Among the numerous "targets" for potential anti-proliferative compounds under investigation are the group of enzymes known as protein kinases.

Cyclin dependent kinases (CDKs) are a type of protein kinase. They are known to be associated with various cyclin subunits, playing pivotal roles in the regulation of a variety of important regulatory pathways in cells, including cell-cycle control, apoptosis, neuronal physiology, differentiation and transcription. There are more than 20 CDKs which may be classified into two major groups, reflecting their functions; namely, the cell cycle regulator CDKs and the transcription regulator CDKs. The class of the cell cycle regulator CDKs includes CDK1, CDK2, CDK3, CDK4 and CDK6, and they function with their cyclin partners (eg cyclin A, B, D1, D2, D3, E and F) to regulate promotion of the cell cycle. The class of the transcription regulator CDKs, includes CDK7, CDK8, CDK9 and CDK11, which work together with cyclin C, H, K, L1, L2, T1 and T2 and tend to play roles in transcriptional regulation. Given the functions of these two CDK classes, it is perhaps not surprising that CDKs have been implicated in cell proliferation diseases and conditions, particularly cancer. Cell proliferation is a result of the direct or indirect deregulation of the cell division cycle and the CDKs play a critical role in the regulation of the various phases of this cycle. Therefore, inhibitors of CDKs and their associated cyclins are considered to be useful targets for cancer therapy.

Certain pyrimidine-based compounds have been previously investigated for use in treating proliferative cell diseases and conditions including cancers, for example, 4-thiazol-2-pyridinylamino-pyrimidines and 5-substituted-4-thiazol-pyrimidines (see International patent publications WO 2005/012298 and WO2013/156780, respectively). These compounds inhibit multiple protein kinases, particularly CDKs, including CDK1/cyclin B, CDK2/cyclin E, CDK2/cyclin A, CDK4/cyclin D1, CDK7/cyclin H and CDK9/cyclin T1.

International patent WO2017/020065 A1 discloses a class of compounds that inhibit the activity of CDK4 and/or CDK6 to inhibit cell proliferation. The inventors further studied and found that the preferred compound N-Cyclopentyl-5-(2-((5-((4-ethylpiperazin-1-yl)methyl) pyridin-2-yl)amino)-5-fluoropyrimidin-4-yl)-4-methylthiazol-2-amine (hereinafter referred to as "Compound A" in this specification) has outstanding activity and can be used as a new generation of CDK4/6 kinase inhibitor.

The abovementioned compound is also described in Chinese patent with Publication No. CN108349964A, and the relevant content of this document can be used as a reference in this application.

However, in the process of drug research, the inventors found that the solubility, stability, oral bioavailability and other aspects of N-Cyclopentyl-5-(2-((5-((4-ethylpiperazin-1-yl)methyl) pyridin-2-yl)amino)-5-fluoropyrimidin-4-yl)-4-methylthiazol-2-amine are unsatisfactory. The inventors worked hard and found that converting N-Cyclopentyl-5-(2-((5-((4-ethylpiperazin-1-yl)methyl) pyridin-2-yl)amino)-5-fluoropyrimidin-4-yl)-4-methylthiazol-2-amine into a corresponding pharmaceutically acceptable salt can solve this problem.

SUMMARY

The first aspect of the present invention relates to a pharmaceutically acceptable salt of N-Cyclopentyl-5-(2-((5-((4-ethylpiperazin-1-yl)methyl) pyridin-2-yl)amino)-5-fluoropyrimidin-4-yl)-4-methylthiazol-2-amine. In any of the aspects described herein, the pharmaceutically acceptable salt may be an inorganic salt. The inorganic salt is preferably hydrochloride, sulfate, phosphate, nitrate, or hydrobromide. In any of the aspects described herein, the pharmaceutically acceptable salt may be an organic salt. The organic salt is preferably maleate, fumarate, citrate, succinate, methanesulfonate, benzenesulfonate, benzoate, p-toluenesulfonate, 1,2-ethanedisulfonate, 2-naphthalenesulfonate, hippurate, glutarate, adipate, ascorbate, malonate, gentisate, nicotinate, L-malate, L-tartrate, or DL-lactate. It is particularly preferred that the pharmaceutically acceptable salt is succinate.

The second aspect of the present invention relates to a method of preparing a pharmaceutically acceptable salt of N-Cyclopentyl-5-(2-((5-((4-ethylpiperazin-1-yl)methyl) pyridin-2-yl)amino)-5-fluoropyrimidin-4-yl)-4-methylthiazol-2-amine. The method may comprise the following steps:

(1) Weighing compound A and succinic acid, wherein the molar ratio of compound A to succinic acid is 1:1 to 1.1;

(2) Adding ethanol to a container containing the compound A and succinic acid of step (1), wherein the amount of ethanol is 1 to 100 times of the total mass of compound A and succinic acid;

(3) Stirring the mixture formed in step (2) under reflux conditions, cooling, and filtering to obtain the succinate Compound A

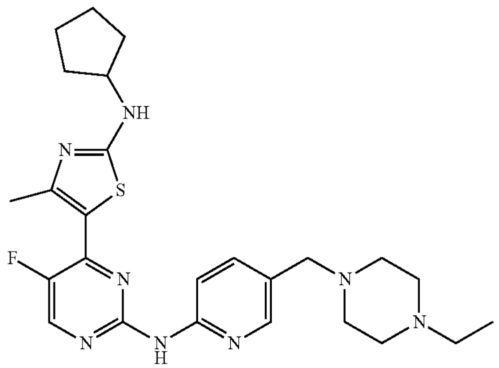

The molar ratio of compound A to succinic acid in step (1) may be 1:1 to 1.05. The amount of ethanol added in step (2) may be 3 to 20 times of the total mass of compound A and succinic acid. The stirring time in step (3) may be 2 to 96 hours.

The third aspect of the present invention relates to a pharmaceutical dosage form, which comprises a pharmaceutically acceptable salt of N-Cyclopentyl-5-(2-((5-((4-ethylpiperazin-1-yl)methyl) pyridin-2-yl)amino)-5-fluoropyrimidin-4-yl)-4-methylthiazol-2-amine and one or more pharmaceutically acceptable carrier.

The fourth aspect of the present invention relates to use of a pharmaceutically acceptable salt of N-Cyclopentyl-5-(2-((5-((4-ethylpiperazin-1-yl)methyl) pyridin-2-yl)amino)-5-fluoropyrimidin-4-yl)-4-methylthiazol-2-amine thereof in the manufacture of a medicament for the treatment of a disease or condition caused by a proliferative disorder.

The fifth aspect of the present invention relates to a method of treating a disease or condition caused by a proliferative disorder, the method comprising administering to a patient in need thereof a pharmaceutically acceptable salt of N-Cyclopentyl-5-(2-((5-((4-ethylpiperazin-1-yl) methyl) pyridin-2-yl)amino)-5-fluoropyrimidin-4-yl)-4-methylthiazol-2-amine.

The sixth aspect of the present invention relates to a pharmaceutically acceptable salt of N-Cyclopentyl-5-(2-((5-((4-ethylpiperazin-1-yl)methyl)pyridin-2-yl)amino)-5-fluoropyrimidin-4-yl)-4-methylthiazol-2-amine for use in treating a disease or condition caused by a proliferative disorder.

The pharmaceutically acceptable salt of N-Cyclopentyl-5-(2-((5-((4-ethylpiperazin-1-yl)methyl) pyridin-2-yl)amino)-5-fluoropyrimidin-4-yl)-4-methylthiazol-2-amine may have an anti-tumor effect by inhibiting protein kinases.

The seventh aspect of the present invention relates to use of N-Cyclopentyl-5-(2-((5-((4-ethylpiperazin-1-yl)methyl) pyridin-2-yl)amino)-5-fluoropyrimidin-4-yl)-4-methylthiazol-2-amine succinate in the manufacture of a medicament for the treatment of a disease or condition caused by a proliferative disorder.

The eighth aspect of the present invention relates to a method of treating a disease or condition caused by a proliferative disorder, the method comprising administering to a patient in need thereof N-Cyclopentyl-5-(2-((5-((4-ethylpiperazin-1-yl)methyl)pyridin-2-yl)amino)-5-fluoropyrimidin-4-yl)-4-meth ylthiazol-2-amine succinate.

The ninth aspect of the present invention relates to N-Cyclopentyl-5-(2-((5-((4-ethylpiperazin-1-yl)methyl) pyridin-2-yl)amino)-5-fluoropyrimidin-4-yl)-4-methylthiazol-2-amine succinate for use in treating a disease or condition caused by a proliferative disorder.

The tenth aspect of the present invention relates to a N-Cyclopentyl-5-(2-((5-((4-ethylpiperazin-1-yl)methyl) pyridin-2-yl)amino)-5-fluoropyrimidin-4-yl)-4-methylthiazol-2-amine succinate designated as Crystal Form A, characterised by one or more of the following: a X-ray powder diffraction pattern with peaks located at positions with 2θ values of about 4.33, 12.98, 16.91, 18.19, 19.08, 19.69, 21.12, 26.21 and 27.38, and a DSC thermogram with a sharp endothermic peak at 221.0° OC.

The X-ray powder diffraction pattern of the Crystal Form A of N-Cyclopentyl-5-(2-((5-((4-ethylpiperazin-1-yl) methyl) pyridin-2-yl)amino)-5-fluoropyrimidin-4-yl)-4-methylthiazol-2-amine succinate may be that shown in FIG. 10.

The eleventh aspect of the present invention relates to a pharmaceutical formulation comprising the Crystal Form A of N-Cyclopentyl-5-(2-((5-((4-ethylpiperazin-1-yl)methyl) pyridin-2-yl)amino)-5-fluoropyrimidin-4-yl)-4-methylthiazol-2-amine succinate and one or more pharmaceutically acceptable excipients.

The twelfth aspect of the present invention relates to use of the Crystal Form A of N-Cyclopentyl-5-(2-((5-((4-ethylpiperazin-1-yl)methyl)pyridin-2-yl)amino)-5-fluoropyrimidin-4-yl)-4-methylthiazol-2-amine succinate in the manufacture of a medicament for the treatment of a disease or condition caused by a proliferative disorder.

The thirteenth aspect of the present invention relates to a method of treating a disease or condition caused by a proliferative disorder, the method comprising administering to a patient in need thereof Crystal Form A of N-Cyclopentyl-5-(2-((5-((4-ethylpiperazin-1-yl)methyl)pyridin-2-yl) amino)-5-fluoropyrimidin-4-yl)-4-methylthiazol-2-amine succinate.

The fourteenth aspect of the present invention relates to Crystal Form A of N-Cyclopentyl-5-(2-((5-((4-ethylpiperazin-1-yl)methyl)pyridin-2-yl)amino)-5-fluoropyrimidin-4-yl)-4-methylthiazol-2-amine succinate for use in treating a disease or condition caused by a proliferative disorder.

In any of the aspects described herein, the disease or condition caused by a proliferative disorder may be cancer. The cancer may be colorectal cancer, breast cancer, cervical cancer, liver cancer, lung cancer, ovarian cancer, neuroendocrine cancer, pancreatic cancer, lymphoma, leukemia, prostate cancer, or brain cancer. The cancer may be colorectal cancer, breast cancer, cervical cancer, liver cancer, lung cancer, ovarian cancer, pancreatic cancer, or brain cancer. The cancer may be brain cancer, colorectal cancer, ovarian cancer, breast cancer, pancreatic cancer, lymphoma, leukemia or prostate cancer. The cancer may be colorectal cancer, breast cancer, cervical cancer, ovarian cancer, or brain cancer.

The fifteenth aspect of the present invention relates to use of N-Cyclopentyl-5-(2-((5-((4-ethylpiperazin-1-yl)methyl) pyridin-2-yl)amino)-5-fluoropyrimidin-4-yl)-4-methylthiazol-2-amine succinate, or the Crystal Form A thereof, in the manufacture of a medicament for inhibiting a protein kinase.

The sixteenth aspect of the present invention relates to a method of inhibiting a protein kinase, the method comprising administering to a patient in need thereof N-Cyclopentyl-5-(2-((5-((4-ethylpiperazin-1-yl)methyl) pyridin-2-yl) amino)-5-fluoropyrimidin-4-yl)-4-methylthiazol-2-amine succinate, or the Crystal Form A thereof.

The seventeenth aspect of the present invention relates to N-Cyclopentyl-5-(2-((5-((4-ethylpiperazin-1-yl)methyl) pyridin-2-yl)amino)-5-fluoropyrimidin-4-yl)-4-methylthiazol-2-amine succinate, or the Crystal Form A thereof, for use in inhibiting a protein kinase.

The eighteenth aspect of the present invention relates to use of N-Cyclopentyl-5-(2-((5-((4-ethylpiperazin-1-yl) methyl) pyridin-2-yl)amino)-5-fluoropyrimidin-4-yl)-4-methylthiazol-2-amine succinate in the preparation of inhibitors of cyclin-dependent kinases (CDKs). The inhibitors may be CDK4/6 inhibitors.

With respect to the free base and other salt forms including hydrochloride, methanesulfonate, phosphate, and the like, the succinate provides many advantages. Compared with the free base, the water solubility of the succinate is improved by 40 times, and it also has a similar solubility improvement in the biological solvent FaSSIF; and the above increase in solubility is not accompanied by a significant increase in hygroscopicity. The hygroscopicity of succinate is significantly lower than that of other salt types, even lower than the free base.

Compared with compound A, the bioavailability of the succinate in animals has been significantly improved due to the increase in solubility. The above and other advantages will be favourable for overcoming various challenges faced by the development of pharmaceutical products containing selective CDK 4/6 kinase inhibitors.

BRIEF DESCRIPTION OF FIGURES

Various features, advantages, and other applications of the present invention will be more obvious with reference to the description below and the accompanying drawings.

DETAILED DESCRIPTION

Figure 1:
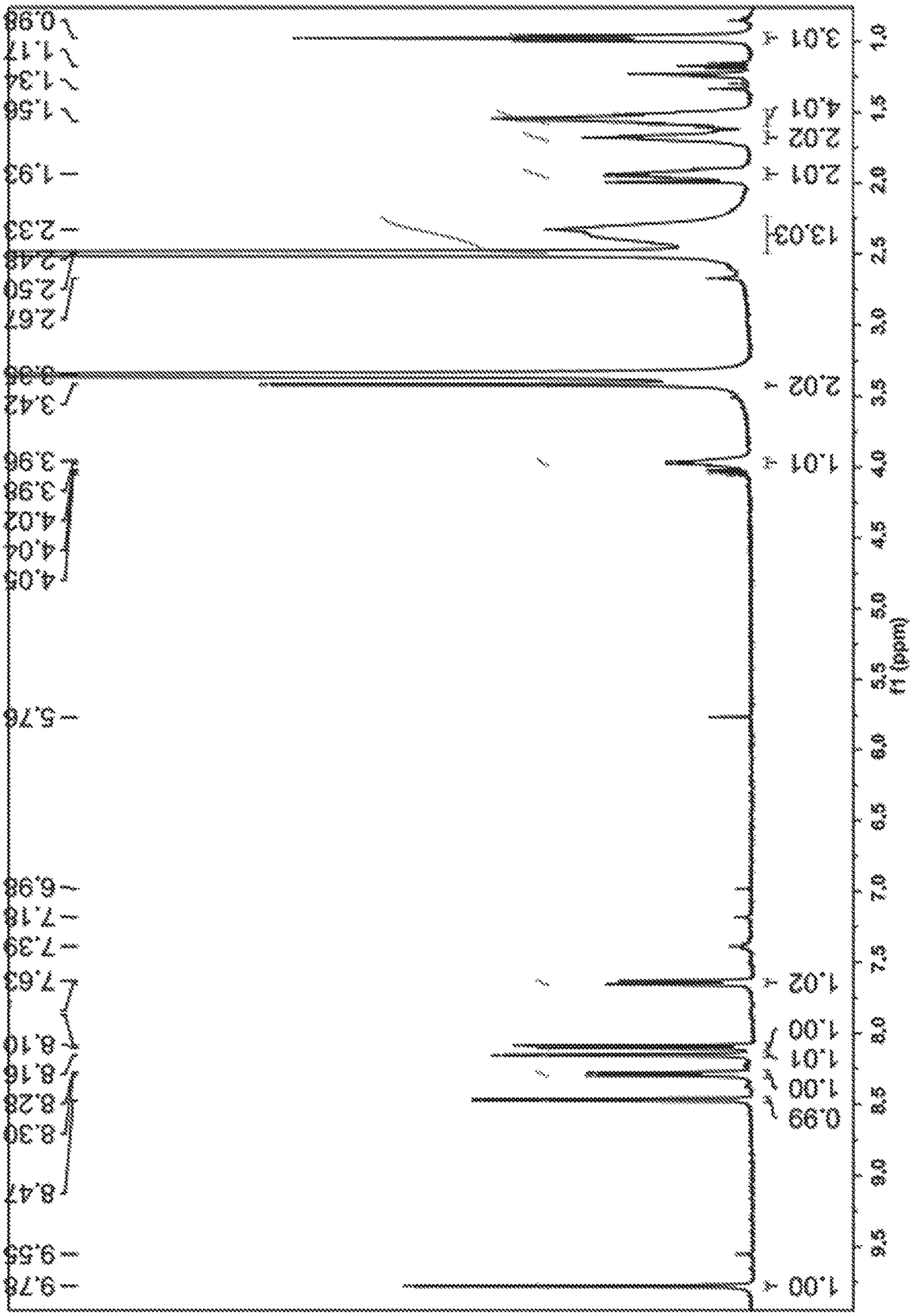
FIG. 1 is a $^1$H NMR spectrum of Compound A.
Figure 2:
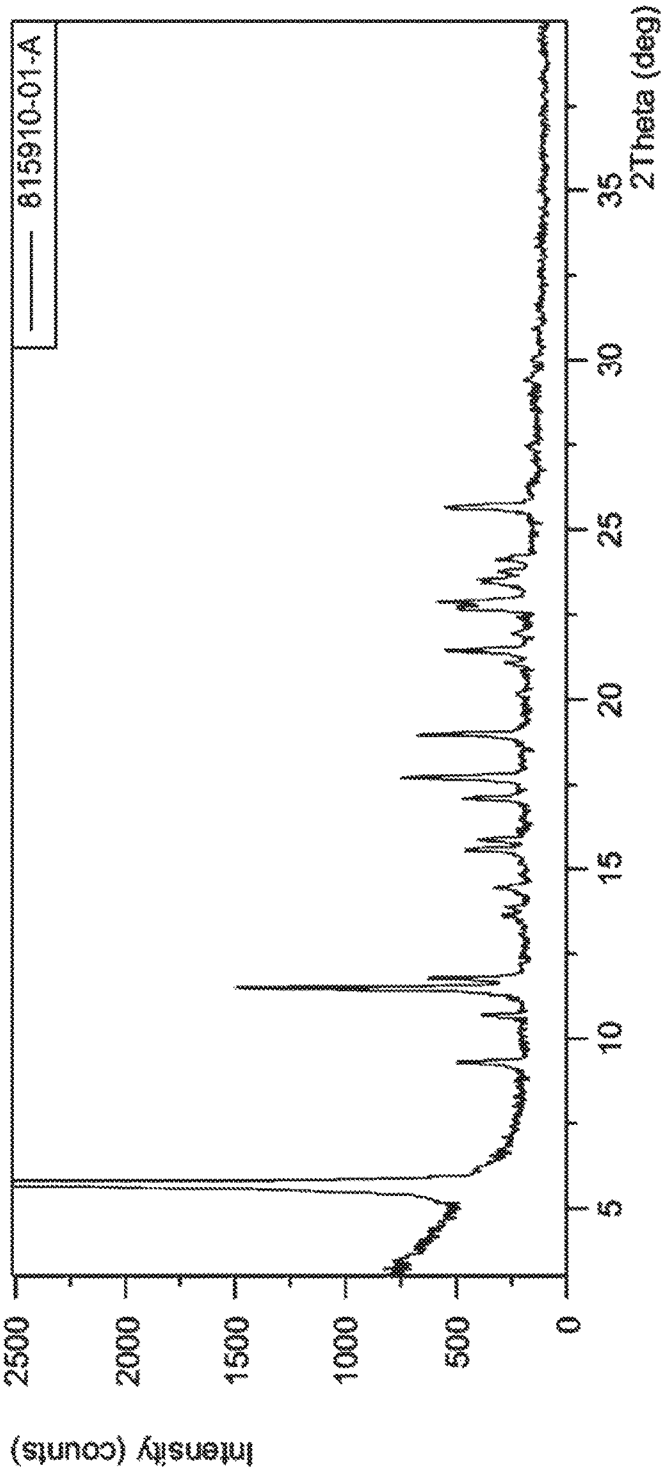
FIG. 2 is the XRPD pattern of Compound A.
Figure 3:
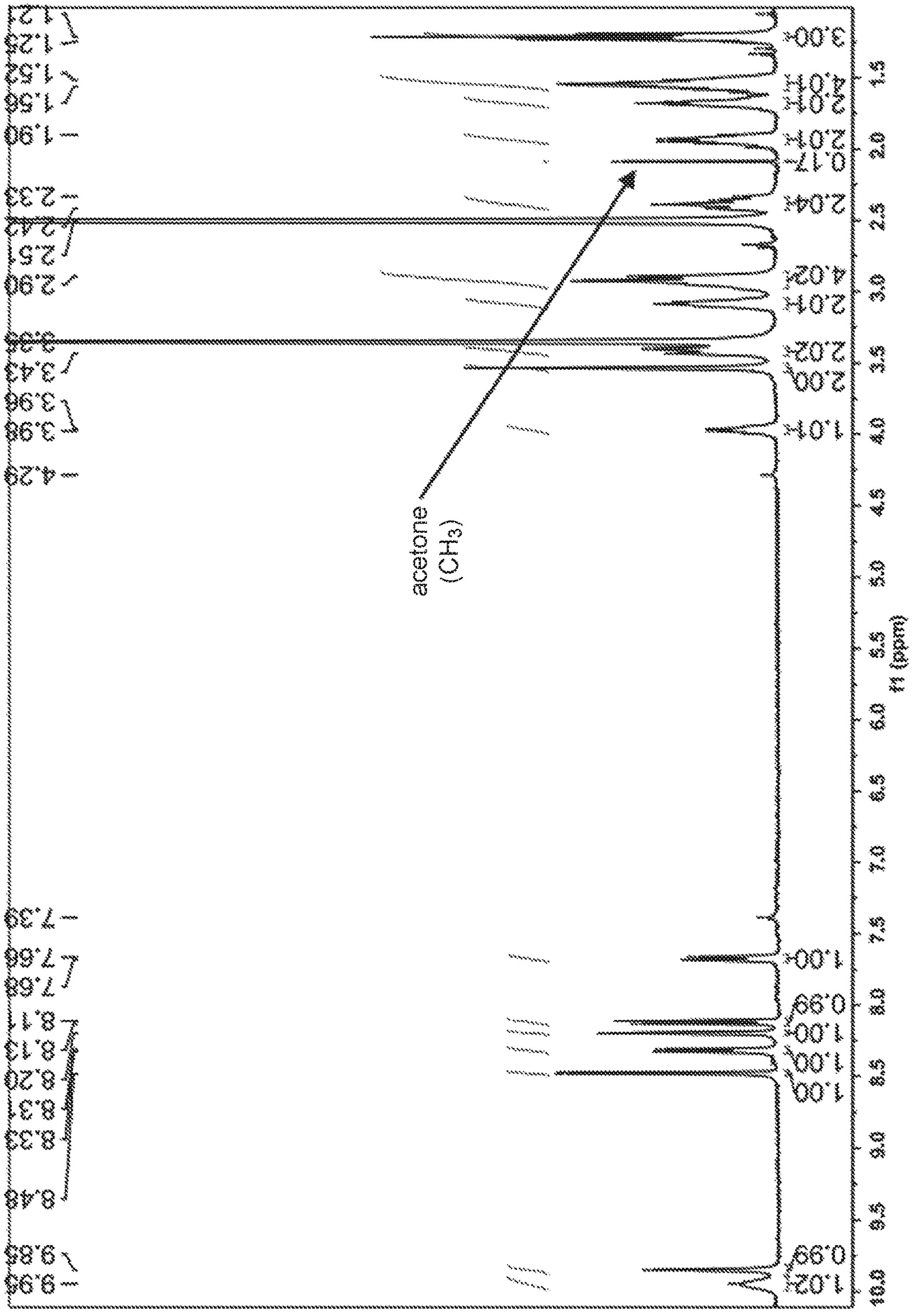
FIG. 3 is a $^1$H NMR spectrum of Compound A hydrochloride.
Figure 4:
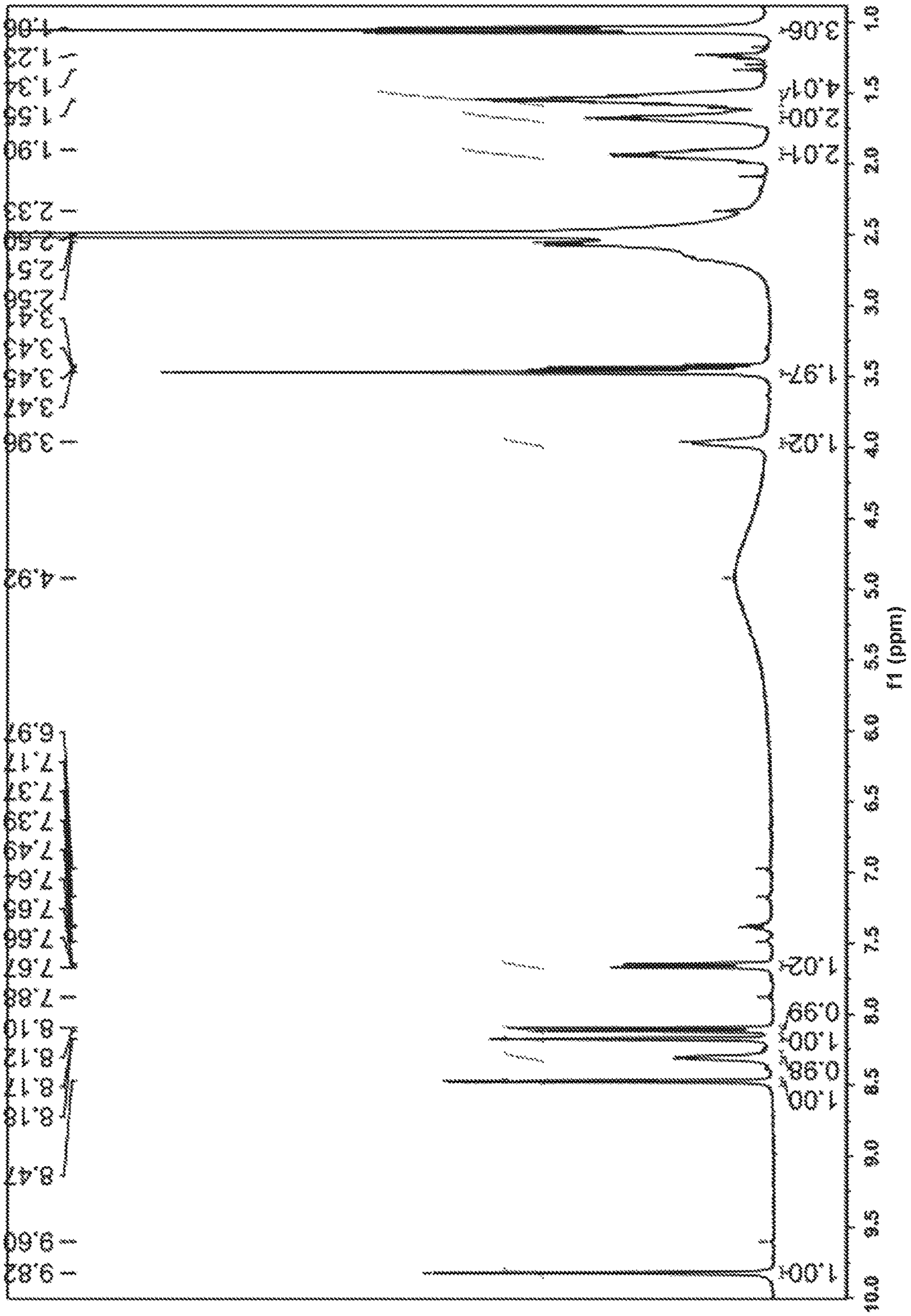
FIG. 4 is a $^1$H NMR spectrum of Compound A phosphate.
Figure 5:
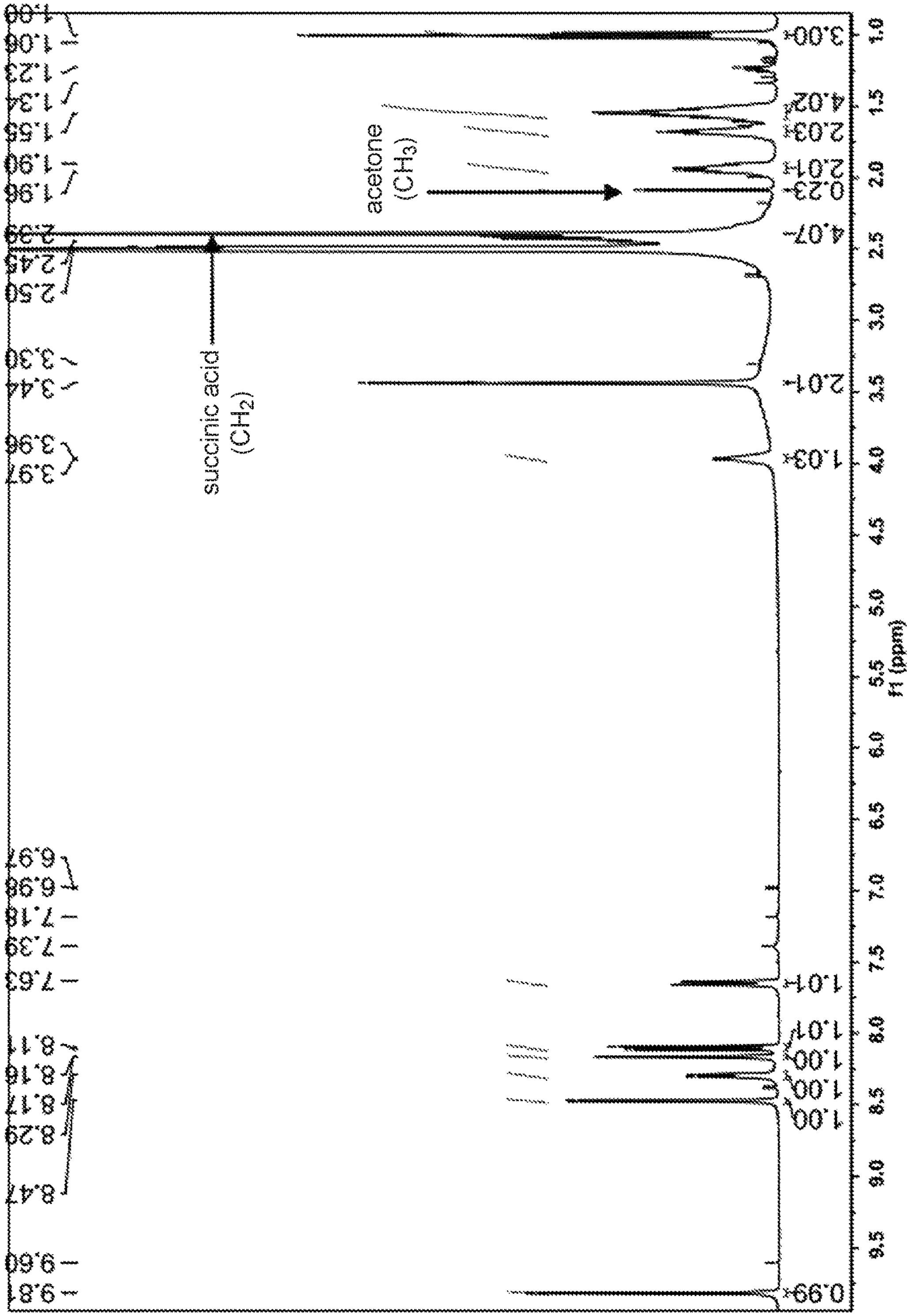
FIG. 5 is a $^1$H NMR spectrum of Compound A succinate.
Figure 6:
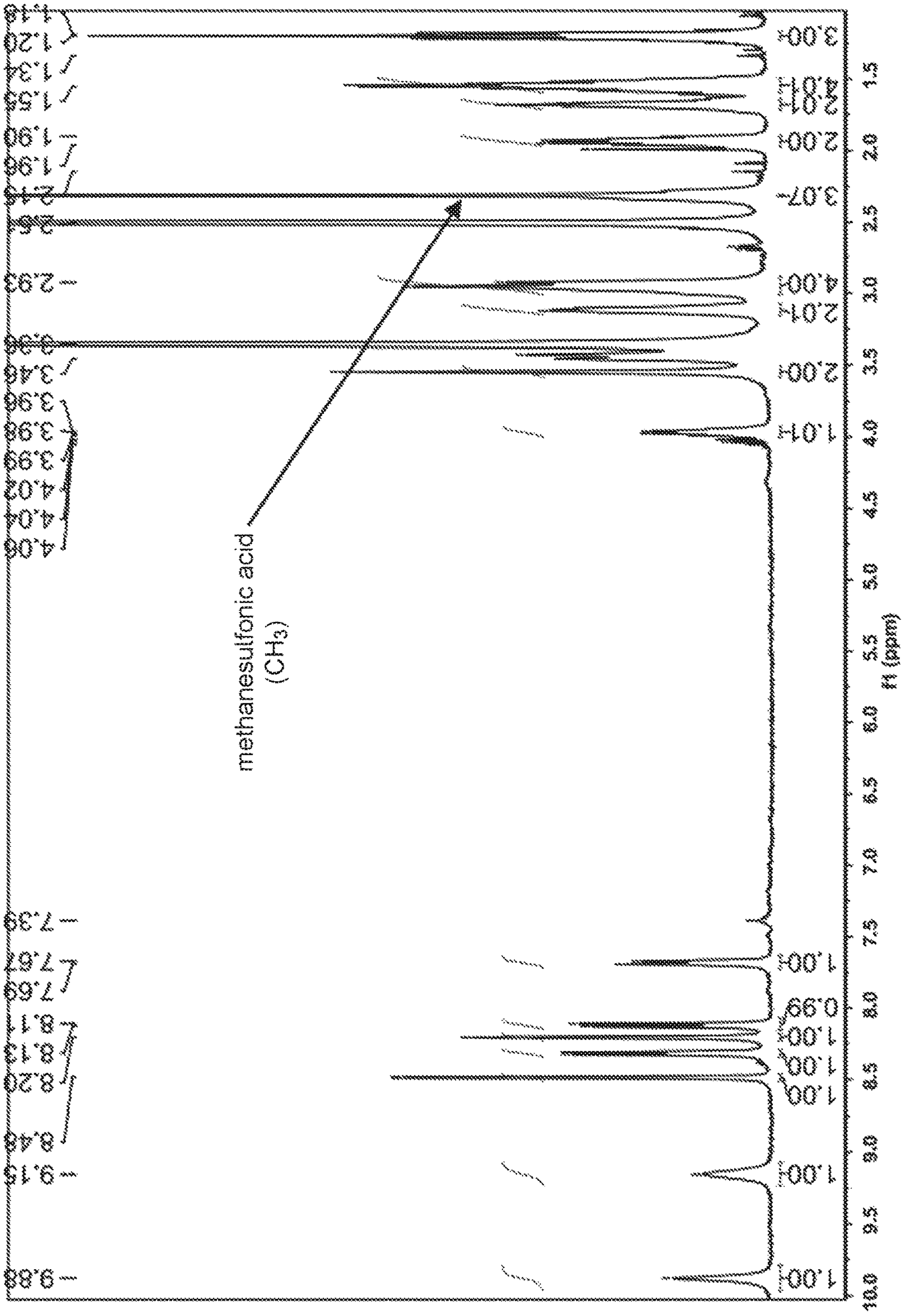
FIG. 6 is a $^1$H NMR spectrum of Compound A mesylate.
Figure 7:
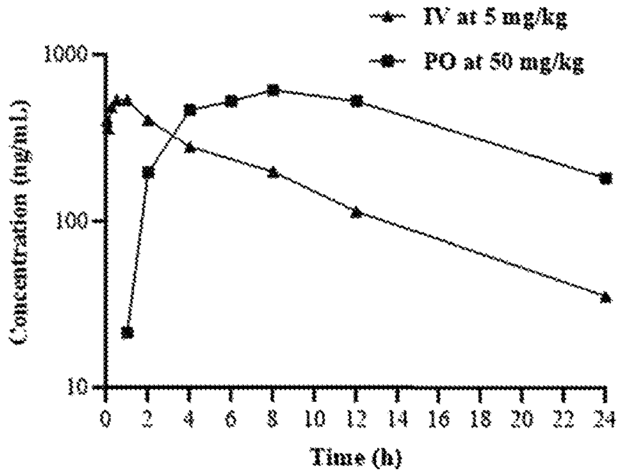
FIG. 7 is a graph showing the pharmacokinetics of Compound A in male cynomolgus monkeys.
Figure 8:
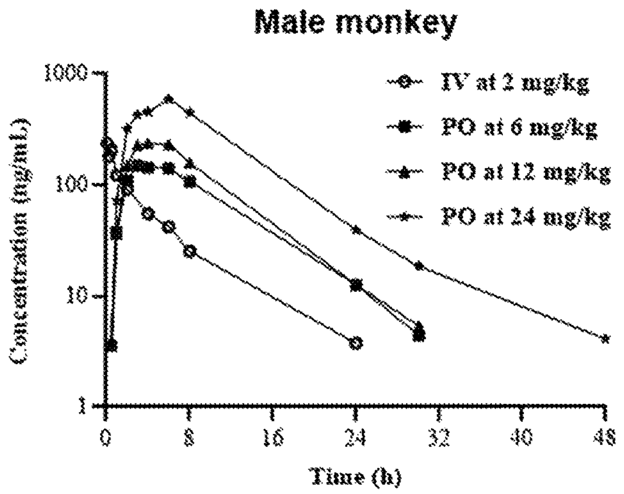
FIG. 8 is a graph showing the pharmacokinetics of Compound A succinate in male cynomolgus monkeys.
Figure 9:
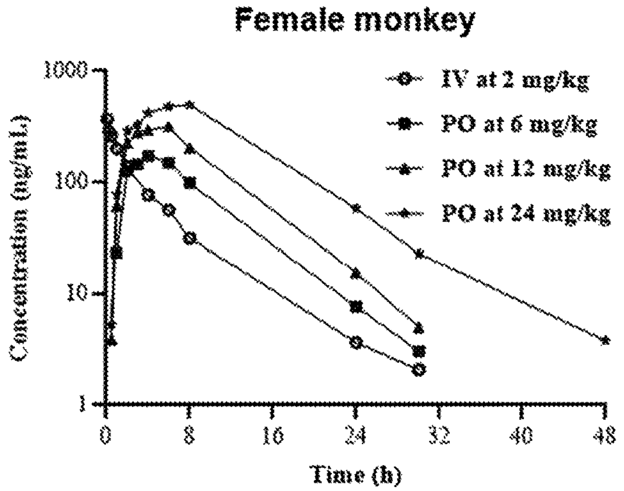
FIG. 9 is a graph showing the pharmacokinetics of compound A succinate in female cynomolgus monkeys.

The present invention will be further described in detail below in conjunction with embodiments, but it is not limited thereto.

Definitions

Diseases and conditions caused by a proliferative disease or disorder that may be treated in accordance with the present disclosure include cancer, such as biliary tract cancer, brain cancer and other cancers of the central nervous system (CNS) (including glioblastomas and medulloblastomas), neuroblastomas, breast cancer, cervical cancer, ovarian cancer (including those arising from epithelial cells, stromal cells, germ cells, and mesenchymal cells), choriocarcinoma, colorectal cancer, endometrial cancer, liver cancer, lung cancer, oesophageal cancer, gastric cancer, haematological neoplasms (including acute lymphocytic leukaemia (ALL)), chronic lymphocytic leukaemia (CLL) and chronic myelogenous leukaemia (CML), and acute myeloid leukaemia (AML), multiple myeloma, AIDS-associated leukaemia's and adult T-cell leukaemia lymphoma, lymphomas (including Non-Hodgkin's lymphoma, Hodgkin's disease and lymphocytic lymphomas)), intraepithelial neoplasms (including Bowen's disease and Paget's disease), oral cancer (including squamous cell carcinoma), pancreatic cancer, prostate cancer, sarcomas (including leiomyosarcoma, rhabdomyosarcoma, liposarcoma, fibrosarcoma, and osteosarcoma), skin cancer (including melanoma, Kaposi's sarcoma, basocellular cancer, and squamous cell cancer), testicular cancer (including germinal tumours such as seminoma, non-seminoma teratomas, and choriocarcinomas), stromal tumours, germ cell tumours, thyroid cancer (including thyroid adenocarcinoma and medullar carcinoma), and renal cancer (including adenocarcinoma and Wilms' tumour).

In some embodiments, the diseases and conditions caused by a proliferative disease or disorder are dependent upon regulatory activity of protein kinases, in particular cyclin dependent kinases (CDKs), such as CDK4/6.

The term "cancer" includes, but is not limited to, the following cancers: leukemia, breast cancer, ovarian cancer, cervical cancer, prostate cancer, testicular cancer, esophageal cancer, gastric cancer, skin cancer, lung cancer, bone cancer, colon cancer, pancreatic cancer, thyroid cancer, biliary tract cancer, throat cancer, lip cancer, tongue cancer, oral cancer, throat cancer, small intestine cancer, colonrectal cancer, colorectal cancer, rectal cancer, brain and central nervous system cancer, malignant glioma, bladder cancer, liver cancer, kidney cancer, lymphoma, and the like. The cancer may be colorectal cancer, breast cancer, cervical cancer, liver cancer, lung cancer, ovarian cancer, neuroendocrine cancer, pancreatic cancer, lymphoma, leukemia, prostate cancer, or brain cancer. The cancer may be breast cancer, brain cancer, cervical cancer, liver cancer, colorectal cancer, lung cancer, ovarian cancer, or pancreatic cancer. The cancer may be brain cancer, colon cancer, ovarian cancer, breast cancer, pancreatic cancer, lymphoma, leukemia or prostate cancer. The cancer may be colorectal cancer, breast cancer, cervical cancer, ovarian cancer, or brain cancer.

In this application, if the chemical name of the compound contradicts the structural formula, the structural formula shall prevail, except for cases where the structural formula has obvious errors.

As used herein, the term "treating" refers to the alleviation of established symptoms of a condition. As such, the act of "treating" a disease or condition therefore includes: (1) delaying the appearance of clinical symptoms of the disease or condition developing in a subject afflicted with the disease or condition; (2) inhibiting the disease or condition (i.e. arresting, reducing or delaying the development of the disease or condition or a relapse thereof (in the case of a maintenance treatment) or at least one clinical or subclinical symptom thereof; and (3) relieving or attenuating the disease or condition (i.e. causing regression of the disease or condition or at least one of its clinical or subclinical symptoms).

The term "pharmaceutically acceptable salt" as used herein, refers to salts that retain the desired biological activity of Compound A, and include pharmaceutically acceptable acid addition salts and base addition salts. Suitable pharmaceutically acceptable acid addition salts may be prepared from an inorganic acid or from an organic acid. Examples of such inorganic acids are hydrochloric, sulfuric, phosphoric, nitric and hydrobromic acid. Appropriate organic acids may be selected from aliphatic, cycloaliphatic, aromatic, heterocyclic carboxylic and sulfonic classes of organic acids, examples of which are formic, acetic, adipic, hippuric, glutaric, propionic, succinic, glycolic, gluconic, lactic, malic, tartaric, citric, ascorbic, gentisic, nicotinic, fumaric, maleic, benzoic, alkyl sulfonic and aryl sulfonic acid. Additional information on pharmaceutically acceptable salts can be found in Remington's Pharmaceutical Sciences, 19th Edition, Mack Publishing Co., Easton, PA 1995.

The pharmaceutically acceptable salt of N-cyclopentyl-5-(2-((5-((4-ethylpiperazin-1-yl)methyl) pyridin-2-yl) amino)-5-fluoropyrimidin-4-yl)-4-methylthiazol-2-amine, as well as N-cyclopentyl-5-(2-((5-((4-ethylpiperazin-1-yl) methyl) pyridin-2-yl)amino)-5-fluoropyrimidin-4-yl)-4-methylthiazol-2-amine succinate and Crystal Form A thereof may be formulated into a pharmaceutical composition with a pharmaceutically acceptable carrier. Examples of suitable carriers are well known to those skilled in the art, and are described in, for example, Remington's Pharmaceutical Sciences, Mack Publishing Co., Easton, PA 1995. Examples of suitable carriers include lactose, starch, glucose, methyl cellulose, magnesium stearate, mannitol, sorbitol and the like. The choice of carrier may be made with regard to the intended route of administration and standard pharmaceutical practice.

A pharmaceutical composition according to the present invention may further comprise any suitable binders, lubricants, suspending agents, coating agents and solubilising agents. Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol. Examples of suitable lubricants include sodium oleate, sodium stearate, magnesium stearate, sodium benzoate, sodium acetate, sodium chloride and the like.

Preservatives, stabilising agents, dyes and even flavouring agents may be provided in the pharmaceutical composition. Examples of preservatives include sodium benzoate, sorbic acid and esters of p-hydroxybenzoic acid. Anti-oxidants and suspending agents may be also used.

A pharmaceutical composition according to the present invention may be adapted for oral, rectal, vaginal, parenteral, intramuscular, intraperitoneal, intraarterial, intrathecal, intrabronchial, subcutaneous, intradermal, intravenous, nasal, buccal or sublingual routes of administration. For oral administration, particular use may be made of compressed tablets, pills, tablets, gellules, drops, and capsules. For other forms of administration, a pharmaceutical composition may comprise solutions or emulsions which may be injected intravenously, intraarterially, intrathecally, subcutaneously, intradermally, intraperitoneally or intramuscularly, and which are prepared from sterile or sterilizable solutions. A pharmaceutical composition according to the present invention may also be in the form of suppositories, pessaries, suspensions, emulsions, lotions, ointments, creams, gels, sprays, solutions or dusting powders. A pharmaceutical composition may be formulated in unit dosage form (i.e. in the form of discrete portions containing a unit dose, or a multiple or sub-unit of a unit dose).

With regard to the novel polymorphic form of N-cyclopentyl-5-(2-((5-((4-ethylpiperazin-1-yl)methyl) pyridin-2-yl)amino)-5-fluoropyrimidin-4-yl)-4-methylthiazol-2-amine succinate "Crystal Form A", it is preferred that this contain 25-100% by weight, especially 50-100% by weight, of the novel form, based on the total amount of N-cyclopentyl-5-(2-((5-((4-ethylpiperazin-1-yl)methyl) pyridin-2-yl)amino)-5-fluoropyrimidin-4-yl)-4-methylthiazol-2-amine succinate. Preferably, such an amount of the novel polymorphic form is 75-100% by weight, especially 90-100% by weight. Highly preferred is an amount of 95-100% by weight.

It will be understood by those skilled in the art that the pharmaceutically acceptable salt of N-cyclopentyl-5-(2-((5-((4-ethylpiperazin-1-yl)methyl) pyridin-2-yl)amino)-5-fluoropyrimidin-4-yl)-4-methylthiazol-2-amine, and/or N-cyclopentyl-5-(2-((5-((4-ethylpiperazin-1-yl)methyl) pyridin-2-yl)amino)-5-fluoropyrimidin-4-yl)-4-methylthiazol-2-amine succinate or Crystal Form A thereof is to be administered or used in an amount sufficient to effect beneficial or desired clinical results. This effective amount can be administered in one or more administrations. Typically, an effective amount is sufficient for treating a disease or condition or otherwise to palliate, ameliorate, stabilise, reverse, slow or delay the progression of a disease or condition such as, for example, a disease or condition caused by a proliferative disorder. By way of example only, an effective amount may comprise between about 0.1 and about 250 mg/kg body weight per day, more preferably between about 0.1 and about 100 mg/kg body weight per day and, still more preferably between about 0.1 and about 25 mg/kg body weight per day. However, notwithstanding the above, it will be understood by those skilled in the art that the effective amount may vary and depend upon a variety of factors including the activity of the particular compound, the metabolic stability and length of action of the particular compound, the age, body weight, sex, health, route and time of administration, rate of excretion of the particular compound, and the severity of, for example, the disease or condition caused by a proliferative disorder to be treated.

The pharmaceutically acceptable salt of N-cyclopentyl-5-(2-((5-((4-ethylpiperazin-1-yl)methyl) pyridin-2-yl) amino)-5-fluoropyrimidin-4-yl)-4-methylthiazol-2-amine, and/or N-cyclopentyl-5-(2-((5-((4-ethylpiperazin-1-yl) methyl) pyridin-2-yl)amino)-5-fluoropyrimidin-4-yl)-4-methylthiazol-2-amine succinate or Crystal Form A thereof is typically applied to the treatment of in a human patient. However, the patient may also be selected from, for example, livestock animals (eg cows, horses, pigs, sheep and goats), companion animals (eg dogs and cats) and exotic animals (eg non-human primates, tigers, elephants etc).

It will be understood by those skilled in the art that the pharmaceutically acceptable salt of N-cyclopentyl-5-(2-((5-((4-ethylpiperazin-1-yl)methyl) pyridin-2-yl)amino)-5-fluoropyrimidin-4-yl)-4-methylthiazol-2-amine, and/or N-cyclopentyl-5-(2-((5-((4-ethylpiperazin-1-yl)methyl) pyridin-2-yl)amino)-5-fluoropyrimidin-4-yl)-4-methylthiazol-2-amine succinate or Crystal Form A thereof may be administered in combination with one or more additional agent(s) for the treatment of diseases and conditions caused by a proliferative disease or disorder, such as cancer. For example, the pharmaceutically acceptable salt of N-cyclopentyl-5-(2-((5-((4-ethylpiperazin-1-yl)methyl) pyridin-2-yl)amino)-5-fluoropyrimidin-4-yl)-4-methylthiazol-2-amine, and/or N-cyclopentyl-5-(2-((5-((4-ethylpiperazin-1-yl)methyl)pyridin-2-yl)amino)-5-fluoropyrimidin-4-yl)-4-methylthiazol-2-amine succinate or Crystal Form A thereof may be used in combination with other anti-cancer agents in order to inhibit more than one cancer signaling pathway simultaneously so as to make cancer cells more susceptible to anti-cancer therapies (e.g. treatment with other anti-cancer agents, chemotherapy, radiotherapy, targeted therapy, immunotherapy or a combination thereof).

Reference to any prior art in this specification is not, and should not be taken as, an acknowledgement or any form of suggestion that such prior art forms part of the common general knowledge.

It will be understood that the terms "comprise" and "include" and any of their derivatives (e.g. comprises, comprising, includes, including) as used in this specification, and the claims that follow, are to be taken to be inclusive of features to which the term refers, and is not meant to exclude the presence of any additional features unless otherwise stated.

EXAMPLES

Example 1

Preparation of Pharmaceutically Acceptable Salts of Compound A

Compound A Hydrochloride

To a mixture of 5 g of compound A and 80 mL of acetone was slowly added 835 μL of hydrochloric acid solution (37% solution); the reaction mixture was stirred at room temperature for 2 days, centrifuged to separate the solid, and dried under vacuum at 50° C. for 3 hours; 4.0 g of compound A hydrochloride was obtained.

Compound A Phosphate

To a suspension of 3.75 g of compound A and 60 mL of ethanol was slowly added 517.5 μL of phosphoric acid solution; the reaction mixture was stirred at room temperature for 2 days, centrifuged to separate the solid, and dried under vacuum at 50° C. for 3 hours; 2.2 g of compound A phosphate was obtained.

Compound A Succinate

A mixture of 106 g of compound A and 25.4 g of succinic acid in 3.07 L of ethanol was heated to reflux and stirred for 4 hours. After cooling, the mixture was filtered. The filter cake was washed with ethanol (20 mL×2) and dried to obtain 122 g of compound A succinate.

Compound A Mesylate

To a solution of 582 mg of methanesulfonic acid and 50 mL of ethyl acetate was added 3.0 g of compound A; the reaction mixture was stirred at room temperature for 2 days, the solid was separated by centrifugation and dried under vacuum at 50° C. for 5 hours; 2.5 g of compound A methanesulfonate was obtained.

Physicochemical Properties of Compound a Salt Forms

TABLE 1

Melting point of Compound A and some of its salt forms

| Sample | Melting point |
|---|---|
| Compound A (free base) | 174.7° C. |
| Hydrochloride | 250.4° C. |
| Phosphate | 218.1° C. |
| Succinate | 219.2° C. |
| Mesylate | 198.6° C. |

The dynamic solubility of Compound A and selected salt forms in biological fluid FaSSIF (simulated fasting state intestinal fluid) and water (1, 2, 4, and 24 hours) were measured at 37° C., and the results are summarized in Table 2. Overall, the solubility of Compound A salt forms of hydrochloride, succinate and methanesulfonate in both FaSSIF and water are significantly increased compared to those of Compound A free base.

TABLE 2

Dynamic solubility of Compound A and some of its salt forms at 37° C.

| | | 1 hour | | 2 hours | | 4 hours | | 24 hours | |
|---|---|---|---|---|---|---|---|---|---|
| Sample | Solvent | S | pH | S | pH | S | pH | S | pH |
| Free base | $H_2O$ | 0.22 | 6.14 | 0.24 | 6.08 | 0.24 | 5.96 | 0.22 | 6.08 |
| Hydrochloride | | 6.8 | 5.56 | 7.1 | 5.56 | 7.2 | 5.58 | 6.8 | 5.51 |
| Phosphate | | 0.45 | 5.39 | 0.41 | 5.69 | 0.44 | 5.46 | 0.36 | 5.24 |
| Succinate | | 2.0 | 4.89 | 2.0 | 4.89 | 2.1 | 4.88 | 2.3 | 4.83 |
| Mesylate | | 8.2 | 5.35 | 8.3 | 5.48 | 8.6 | 5.39 | 8.5 | 5.38 |
| Free base | FaSSIF | 0.27 | 6.48 | 0.28 | 6.48 | 0.24 | 6.49 | 0.20 | 6.47 |
| Hydrochloride | | 2.0 | 6.43 | 2.0 | 6.39 | 2.2 | 6.41 | 2.1 | 6.42 |
| Phosphate | | 1.7 | 6.36 | 0.67 | 6.39 | 0.47 | 6.42 | 0.33 | 6.38 |
| Succinate | | 8.2 | 5.31 | 8.1 | 5.31 | 8.1 | 5.30 | 1.1 | 5.31 |
| Mesylate | | 8.8 | 6.30 | 8.3 | 6.26 | 8.4 | 6.31 | 4.4 | 6.53 |

S: Solubility (mg/mL)

Compound A salts and Compound A were tested for their solid-state stability under the conditions of 25° C./60% RH and 40° C./75% RH. After 14 days, the samples were analyzed by HPLC and the results demonstrated that Compound A salts and Compound A were stable (Table 3).

TABLE 3

Stability of Compound A and some of its salt forms

| | | | 14-days stability data | |
|---|---|---|---|---|
| Sample | Initial purity (area %) | Evaluation conditions | Purity (area %) | Relative purity (% of initial) |
| Free base | 97.6 | 25° C./60% RH | 97.6 | 100.0 |
| | | 40° C./75% RH | 97.6 | 100.1 |
| Hydrochloride | 97.7 | 25° C./60% RH | 97.6 | 99.9 |
| | | 40° C./75% RH | 97.7 | 100.0 |
| Phosphate | 98.3 | 25° C./60% RH | 98.3 | 100.0 |
| | | 40° C./75% RH | 98.2 | 99.9 |
| Succinate | 97.9 | 25° C./60% RH | 97.9 | 100.0 |
| | | 40° C./75% RH | 97.9 | 100.0 |
| Mesylate | 97.5 | 25° C./60% RH | 97.6 | 100.1 |
| | | 40° C./75% RH | 97.5 | 100.0 |

Dynamic moisture adsorption (DVS) was used to evaluate the hygroscopicity of compound A and salt forms under the condition of 25° C. and 80% RH. The results are shown in Table 4. Compound A succinate showed a minimal hygroscopicity.

TABLE 4

| Hygroscopicity of Compound A and some of its salt forms | | |
|---|---|---|
| Samples | Moisture absorbed at 25° C./80% RH (%) | Hygroscopicity |
| Free base | 1.4 | Slightly hygroscopic |
| Hydrochloride | 3.4 | Hygroscopic |
| Phosphate | 3.7 | Hygroscopic |
| Succinate | 1.1 | Slightly hygroscopic |
| Mesylate | 14.4 | Extremely hygroscopic |

Example 2 In Vitro Anti-Proliferative Activity of Compound A Succinate

The thymidine incorporation (3H-TdR) assay was used to assess the anti-proliferative effect of the Compound A succinate on tumor cell lines. The cells were treated with a series of concentrations of Compound A succinate for 24 hours; 3H-TdR was added, and the cells were continued in the incubator for further 48 hours. Scintillation fluid was added, read on a liquid scintillation counter, and the inhibiting cell growth by 50% ($IC_{50}$) was calculated as shown in Table 5.

TABLE 5

| Anti-proliferative activity of Compound A succinate | | |
|---|---|---|
| Cancer cell lines | Types | $IC_{50}$ (nM) |
| U-87MG | Brain tumor | 42.57 |
| COLO-205 | Colon cancer | 839.1 |
| SK-OV-3 | Ovarian cancer | 811.6 |
| ZR-75-1 | Breast cancer | 35.72 |
| MDA-MB-435S | Breast cancer | 37.28 |
| PANC-1 | Pancreatic cancer | 811.6 |
| Raji | Lymphoma | 608.4 |
| MOLM-13 | Leukemia | 259.9 |
| MV-4-11 | Leukemia | 88.77 |
| PC-3 | Prostate cancer | 167.9 |

Example 3 In Vivo Anti-Tumor Efficacy of Compound a Succinate

Compound A succinate was also assessed for in vivo anti-tumor activity in subcutaneous xenografts. Briefly, female BALB/c nude mice were inoculated with A2780 ovarian cancer cells; when the mean tumour volume reached 150-200 $mm^3$, animals were randomized to groups. The animals (n=8 per group) were treated orally with vehicle (ultra-pure water), Compound A succinate (62.5, 125 or 250 mg/kg), or Palbociclib (75 mg/kg) once a day for 14 consecutive days. Mice were observed daily for signs of toxicity and weight loss, and tumour volume measured every other day. Tumour dimensions were measured with automatic callipers and volumes calculated using the formula: $Vol=0.52 \times L \times W^2$, where L and W are perpendicularly measured diameters with L≥W. Compound A succinate markedly reduced tumor growth compared to vehicle treatment with a tumor growth inhibition (T/C %) of 44.8, 70.8, 86.2 and 42.8 at doses of 62.5, 125 and 250 mg/kg, respectively, on day 14. Palbociclib was efficacious at 75 mg/kg, resulting in T/C of 42.8% (Table 6).

TABLE 6

| In vivo anti-tumor efficacy of Compound A succinate in ovarian cancer xenograft | | | |
|---|---|---|---|
| Group, mg/kg | | Tumor volume (±S, $mm^3$) | Mean tumor growth inhibition (T/C, %) |
| Vehicle | — | 3135.7 ± 246.5 | — |
| Compound A | 62.5 | 1789.5 ± 131.5 | 44.8 |
| Succinate | 125 | 1009.6 ± 87.0 | 70.8 |
| | 250 | 546.4 ± 71.1 | 86.2 |
| Palbociclib | 75 | 1850.1 ± 121.1 | 42.79 |

A separate study of Compound A succinate was conducted in COLO 205 colorectal tumor xenograft. The tumor-bearing mice (n=8) were treated orally with vehicle (ultra-pure water), or Compound A succinate (50 or 100 mg/kg) once daily for 21 days. As a positive control chemotherapy 5-FU (15 mg/kg) was given intraperitoneally. Compound A succinate demonstrated marked anti-tumor efficacy with T/C %=36.3 and 74.7 at doses of 50 and 100 mg/kg, respectively, on day 21. 5-FU was also effective with a T/C=47.2% (Table 7).

TABLE 7

| In vivo anti-tumor efficacy of Compound A succinate in colorectal cancer xenograft | | | | |
|---|---|---|---|---|
| Group (mg/kg) | | Number of animals | Tumor volume (±S, $mm^3$) | Inhibition of tumor growth (T/C, %) |
| Solvent control | — | 8 | 1410.72 ± 136.44 | — |
| compound A | 50 | 8 | 941.10 ± 80.90 | 36.26 |
| Succinate | 100 | 8 | 443.72 ± 40.49 | 74.69 |
| 5-FU | 15 | 8 | 799.62 ± 61.95 | 47.20 |

Example 4 Pharmacokinetic (PK) Study

Two groups of male cynomolgus monkeys (n=3 per group) were given Compound A by a single intravenous injection (i.v.) of 5 mg/kg, or intragastric administration (i.g.) of 50 mg/kg. Blood samples were collected at different time points. The exposure of Compound A in plasma samples were measured by LC-MS/MS method, and PK parameters (Table 8) were calculated using Phoenix WinNonlin 8.0 software.

TABLE 8

| Pharmacokinetic parameters of Compound A | | | | | | | | | |
|---|---|---|---|---|---|---|---|---|---|
| Route of administration | Dosage mg/kg | No. animals | $T_{1/2}$ h | $C_{max}$ ng/ml | $AUC_{(0-t)}$ h*ng/ml | $AUC_{(0-\infty)}$ h*ng/mL | Vd L/kg | Cl ml/min/kg | F % |
| i.v. | 5 | 3 | 6.5 | 447 | 4187 | 4560 | 9.8 | 19.4 | — |
| i.g. | 50 | 3 | 8.3 | 643 | 9543 | 7305 | — | — | 21.8 |

In a separate study, four cynomolgus monkeys were divided into two groups (n=2 per group), and given Compound A succinate at 2 mg/kg by i.v. and 24 mg/kg by i.g., respectively. The plasma samples were collected, analyzed and PK parameters were calculated as above. Compound A succinate has shown the improved PK profiles compared to Compound A; the bioavailability of compound A succinate in female and male cynomolgus monkeys was F=72.8% and 54.9% (Table 9) compared to the F=21.8% of Compound A free base at 50 mg/kg.

TABLE 9

Pharmacokinetic parameters of Compound A succinate

| Route of administration | Dosage mg/kg | Sex | $T_{1/2}$ h | $C_{max}$ ng/mL | $AUC_{(0-t)}$ h*ng/mL | $AUC_{(0-\infty)}$ h*ng/mL | Vz mL/kg | Cl mL/h/kg | F % |
|---|---|---|---|---|---|---|---|---|---|
| i.v. | 2 | male | 5.3 | 240 | 843 | 872 | 17715 | 2347 | — |
| | | female | 4.7 | 371 | 1168 | 1186 | 13230 | 1859 | — |
| i.g | 24 | male | 6.0 | 593 | 7370 | 7420 | — | — | 72.8 |
| | | female | 6.0 | 532 | 7704 | 7738 | — | — | 54.9 |

Example 5 the Crystal Forms of Compound A Succinate

Figure 10:
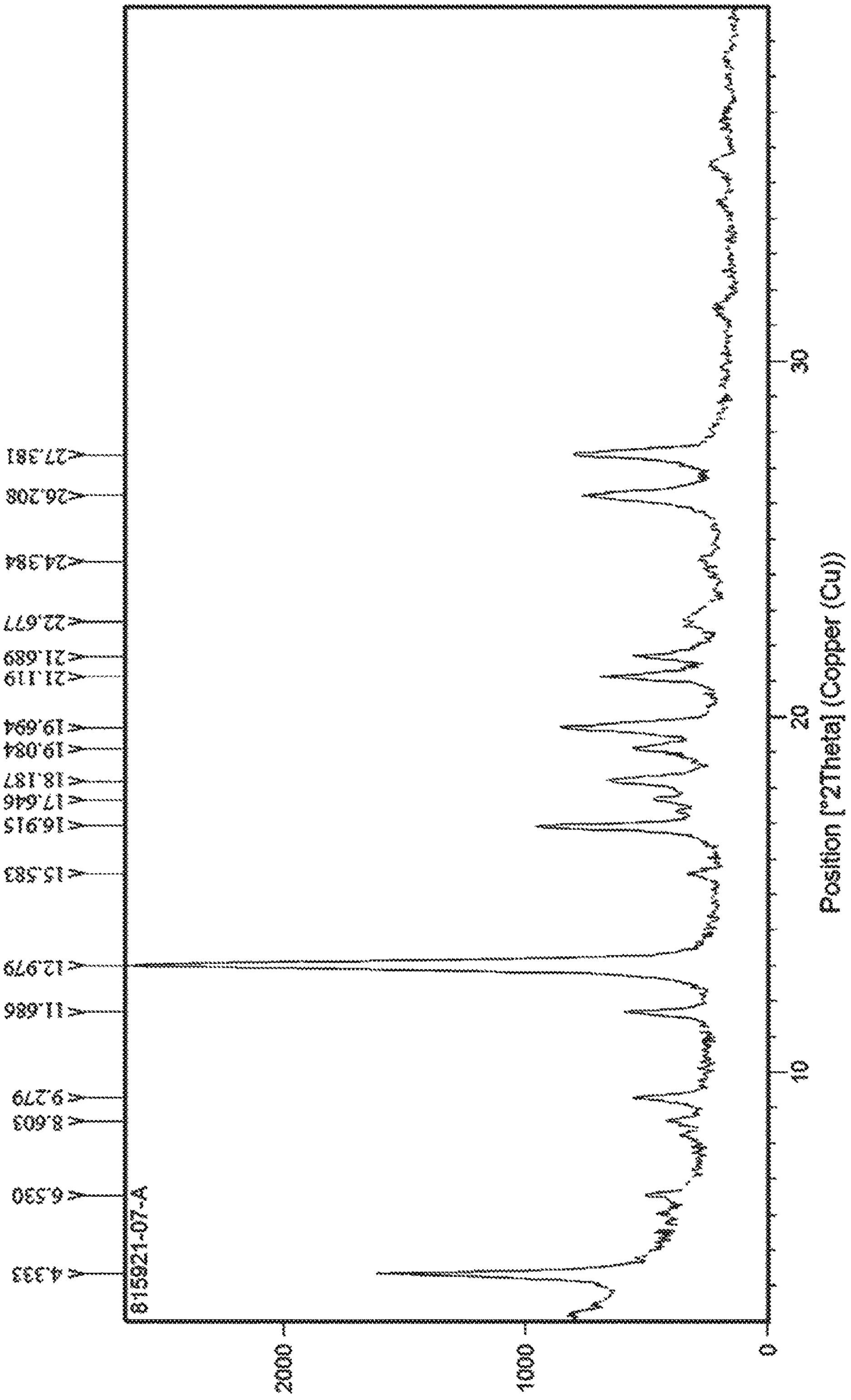
FIG. 10 is an XRPD pattern of Compound A succinate crystal form A.
Figure 11:
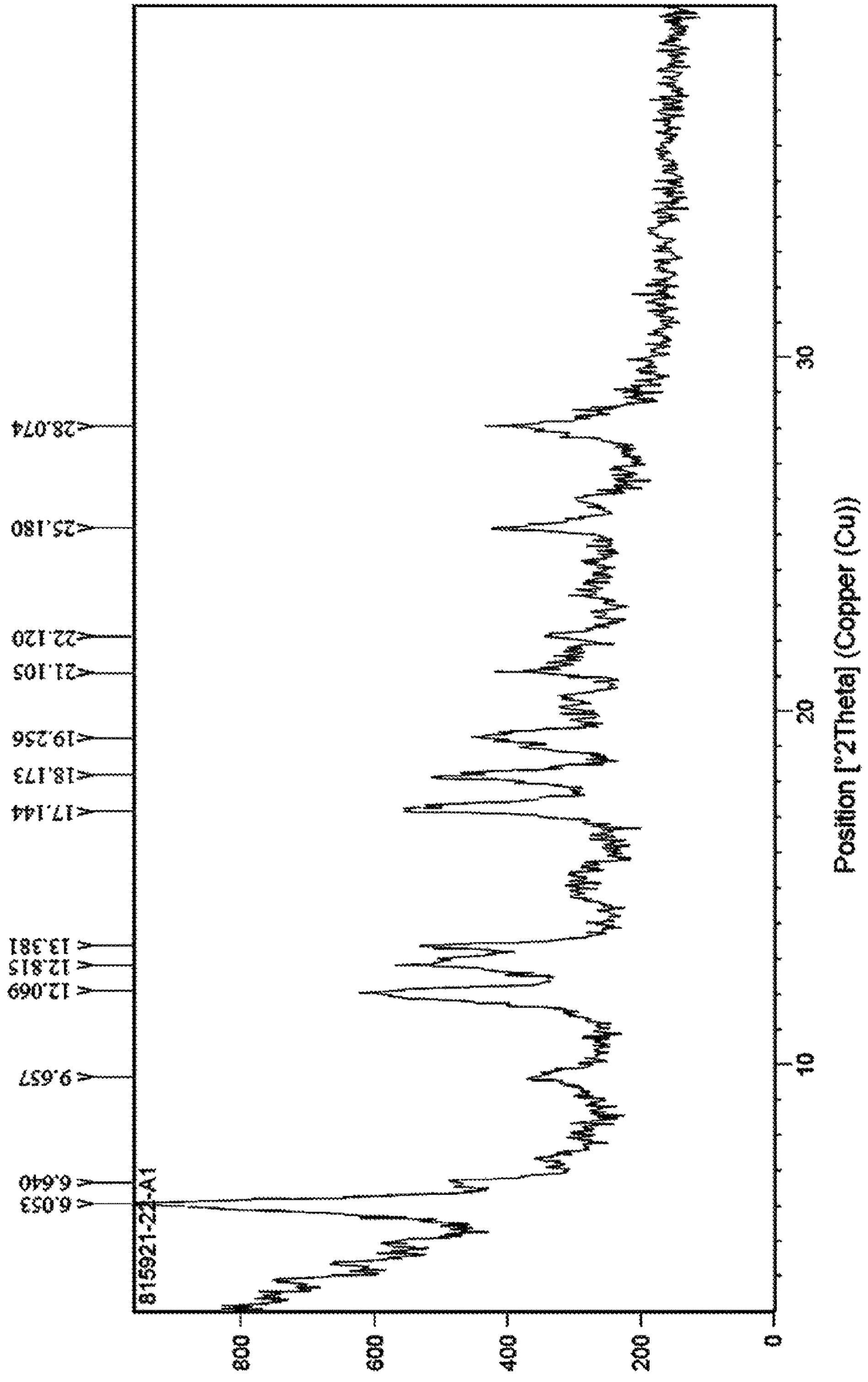
FIG. 11 is an XRPD pattern of Compound A succinate crystal form B.
Figure 12:
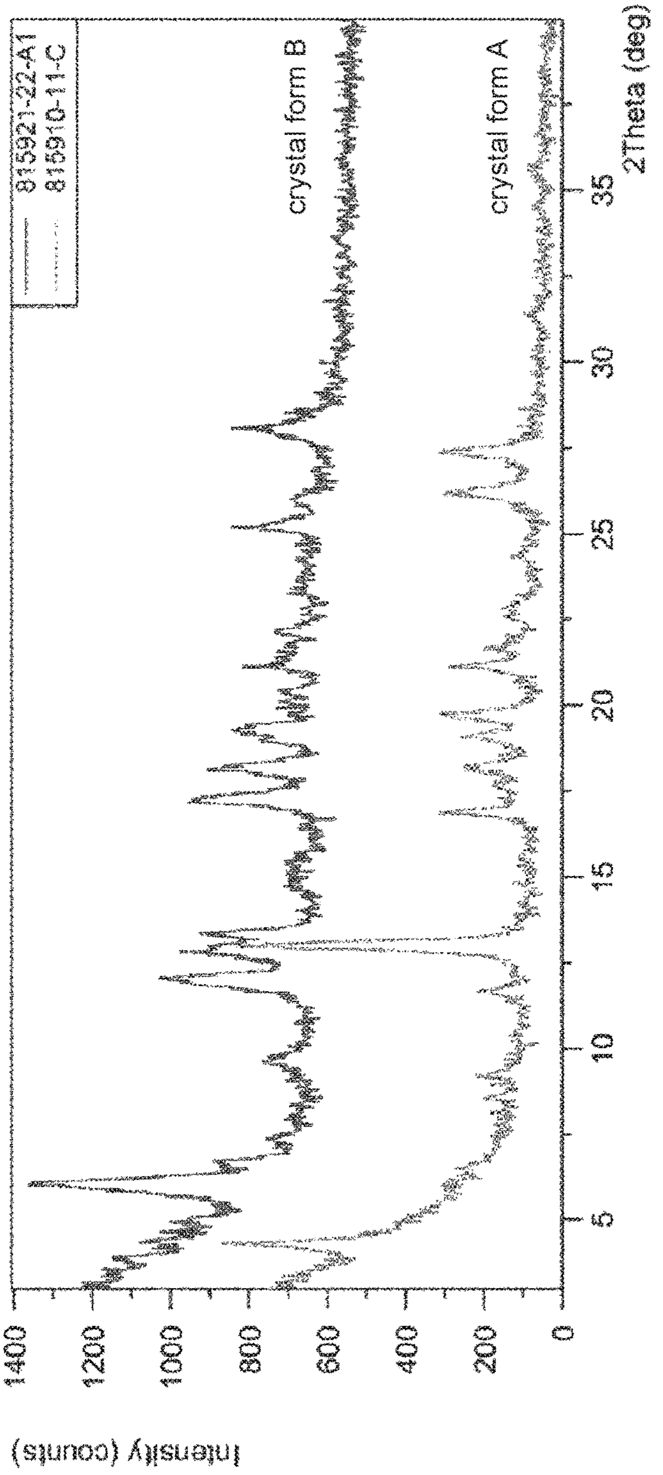
FIG. 12 is an XRPD overlay pattern of the Compound A succinate crystal forms A and B.

The polymorphic screening of Compound A succinate was carried out. The crystal form A of Compound A succinate was prepared by suspending and stirring of Compound A with succinic acid in acetone. It was found that Compound A succinate can exist in two different crystal forms, i.e., crystal form A and crystal form B. The X-ray Powder Diffraction (XRPD) overlays of crystal form A, crystal form B, and crystal form A/B are shown in FIGS. 10-12.

Preparation of Crystal Form A

A mixture of Compound A in ethanol (1:23.25, w/w) was added succinic acid (0.24×Compound A, w/w), and heated at reflux for 4 hours. Upon cooling to 5-10° C., the mixture was filtered. The solid was washed with an appropriate amount of ethanol and dried at 60±5° C. to obtain the crystal form A of Compound A succinate as an off-white solid.

Preparation of Crystal Form B

Figure 13:
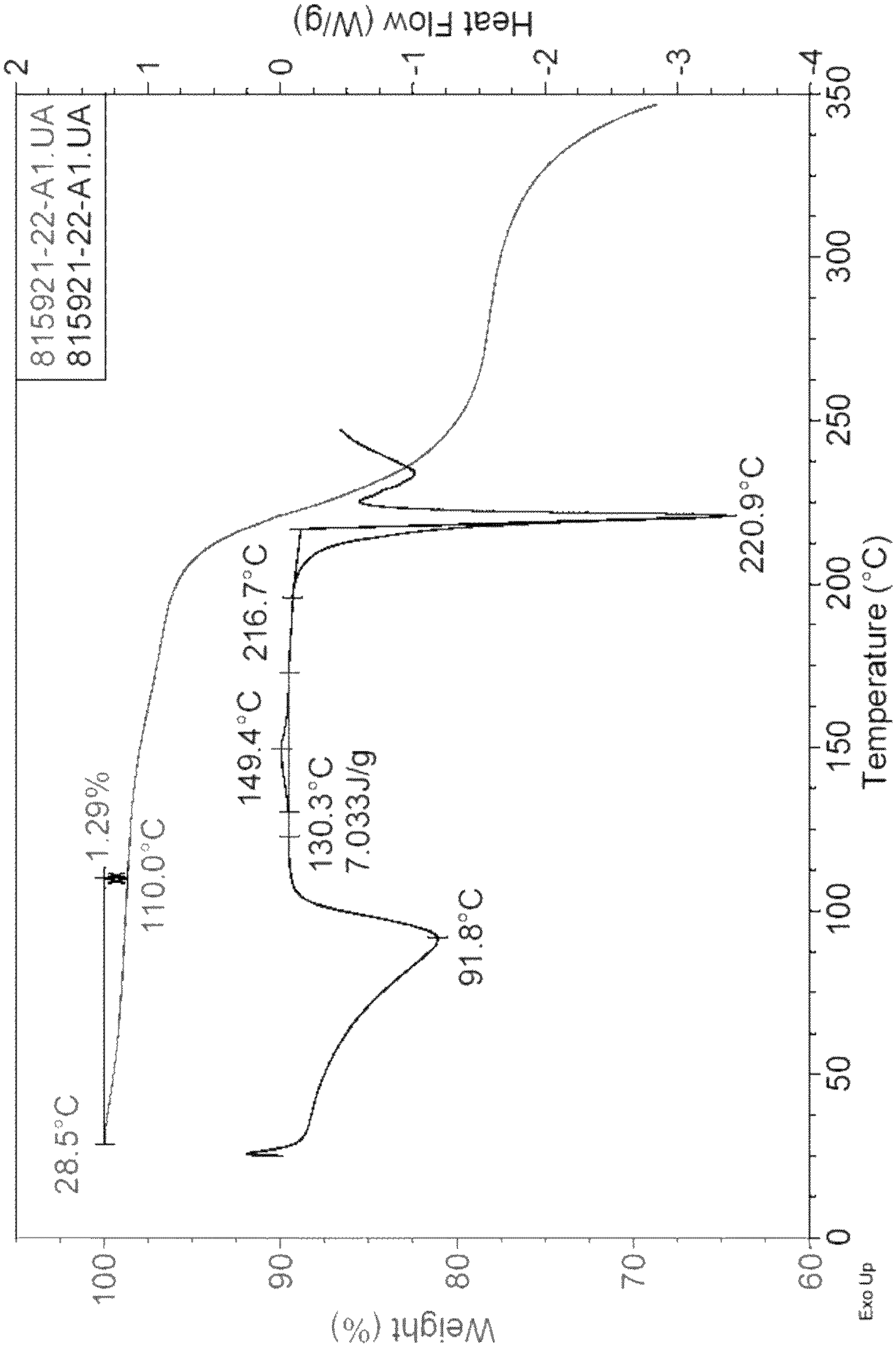
FIG. 13 is a DSC thermogram of Compound A succinate crystal form B.

Crystal form B is transformed from crystal form A by slowly lowering the temperature in a mixture of MeOH/$CHCl_3$ (1:6, v/v) and evaporating the solvent. The XRPD data of the sample was obtained; TGA/DSC results, as seen in FIG. 13, show that the sample has a weight loss of 1.3% when heated from room temperature to 110° C. (theoretical weight loss of monohydrate is about 2.8%; theoretical weight loss of hemihydrate is about 1.4%), and a broad endothermic peak at 91.8° C. (peak temperature), a weakly broad exothermic peak at 149.4° C. (peak temperature), and a sharp endothermic peak at 220.9° C. (peak temperature) were observed. $^1$H NMR showed that the molar ratio of Compound A succinic acid to Compound A free base was 1:1.

Thermodynamic stability of crystal form A and crystal form B was studied in EtOH and THF at room temperature and 50° C., respectively. The results showed that crystal form B was converted to crystal form A in all experiments. In a mixture of EtOH/$H_2O$ or in water at room temperature the crystal form B was also converted to crystal form A. The study demonstrated that the anhydrous crystal form A is thermodynamically more stable from room temperature to 50° C. compared to crystal form B.

The inventors surprisingly discovered that succinate has improved performance in terms of solubility, hygroscopicity and bioavailability, and crystal form A is a thermodynamically stable crystal form.

All reference documents mentioned in the present invention are referenced in the present application, as if each reference document is individually referenced.

It will be appreciated by those skilled in the art that the disclosure is not restricted in its use to the particular application or applications described. Neither is the present disclosure restricted in its preferred embodiment with regard to the particular elements and/or features described or depicted herein. It will be appreciated that the disclosure is not limited to the embodiment or embodiments disclosed, but is capable of numerous rearrangements, modifications and substitutions without departing from the scope as set forth and defined by the following claims.

The invention claimed is:

1. N-Cyclopentyl-5-(2-((5-((4-ethylpiperazin-1-yl)methyl)pyridin-2-yl)amino)-5-fluoropyrimidin-4-yl)-4-methylthiazol-2-amine succinate.

2. A pharmaceutical formulation comprising the succinate of claim 1 and one or more pharmaceutically acceptable excipients.

3. Crystal Form A of the succinate of claim 1 having an X-ray powder diffraction pattern with peaks located at positions with 2Θ values of about 4.33, 12.98, 16.91, 18.19, 19.08, 19.69, 21.12, 26.21 and 27.38.

4. The Crystal Form A of claim 3, wherein the X-ray powder diffraction pattern is as represented by FIG. 10.

5. The Crystal Form A of claim 3, having a DSC thermogram with a sharp endothermic peak at 221.0° C.

6. A pharmaceutical formulation comprising Crystal Form A of a succinate of claim 3 and one or more pharmaceutically acceptable excipients.

7. A method of preparing the succinate of claim 1, the method comprising the following steps:

(1) weighing compound A and succinic acid, wherein the molar ratio of compound A to succinic acid is 1:1 to 1.1;

(2) adding ethanol to a container containing the compound A and succinic acid of step (1), wherein the amount of ethanol is 1 to 100 times of the total mass of compound A and succinic acid;

(3) stirring the mixture formed in step (2) under reflux conditions, cooling, and filtering to obtain the succinate Compound A

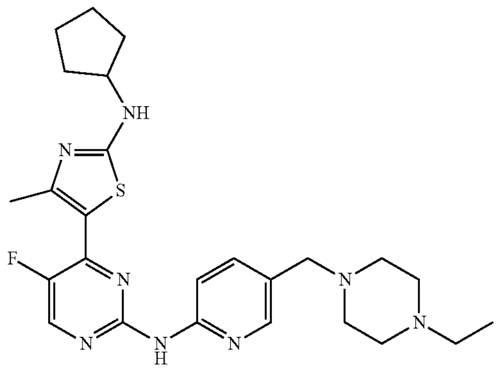

8. The method of claim 7, wherein the molar ratio of compound A to succinic acid in step (1) is 1:1 to 1.05.

9. The method of claim 7, wherein the amount of ethanol added is 3 to 20 times of the total mass of compound A and succinic acid in step (2).

10. The method of claim 7, wherein the stirring time in step (3) is 2 to 96 hours.

11. A method of treating a cancer, wherein the cancer is colorectal cancer, breast cancer, cervical cancer, liver cancer, lung cancer, ovarian cancer, pancreatic cancer, lymphoma, leukemia, prostate cancer, or brain cancer, the method comprising administering to a patient in need thereof the succinate of claim 1.

12. A method of inhibiting CDK 4/6 in a subject in need thereof, wherein the subject has a cancer selected from the group consisting of colorectal cancer, breast cancer, cervical cancer, liver cancer, lung cancer, ovarian cancer, pancreatic cancer, lymphoma, leukemia, prostate cancer, or brain cancer, comprising administering to the subject N-Cyclopentyl-5-(2-(5-((4-ethylpiperazin-1-yl)methyl)pyridin-2-yl) amino)-5-fluoropyrimidin-4-yl)-4-methylthiazol-2-amine succinate.

* * * * *